United States Patent [19]

Tucker

[11] Patent Number: 4,798,702
[45] Date of Patent: Jan. 17, 1989

[54] STERILIZER UNIT FOR FLUID MEDIA AND PROCESS

[76] Inventor: Robert E. Tucker, P. O. Box 414, Florissant, Mo. 63032

[21] Appl. No.: 906,030

[22] Filed: Sep. 10, 1986

[51] Int. Cl.$^4$ .................. G01N 23/10; G01N 23/12
[52] U.S. Cl. ........................... 422/24; 422/198; 210/748; 250/437; 250/438; 250/504 R
[58] Field of Search ............ 422/24, 46, 80, 198, 422/186, 200, 201, 307, 312; 210/85, 195.1, 259, 295, 748; 250/435–438, 504 R

[56] References Cited

U.S. PATENT DOCUMENTS

| | | | |
|---|---|---|---|
| 2,935,611 | 5/1960 | Myers | 250/435 |
| 3,550,782 | 12/1970 | Veloz | 422/24 |
| 3,566,105 | 2/1971 | Wiltrout et al. | 250/435 |
| 3,700,406 | 10/1972 | Landry | 422/24 |
| 3,894,236 | 7/1975 | Hazelrigg | 250/435 |
| 4,400,270 | 8/1983 | Hillman | 250/437 |

FOREIGN PATENT DOCUMENTS

| | | | |
|---|---|---|---|
| 674555 | 11/1963 | Canada | 250/435 |
| 881096 | 5/1952 | Fed. Rep. of Germany | 250/435 |
| 910777 | 3/1954 | Fed. Rep. of Germany | 250/435 |
| 707575 | 4/1954 | United Kingdom | 250/437 |

*Primary Examiner*—Barry S. Richman
*Assistant Examiner*—Lynn M. Kummert
*Attorney, Agent, or Firm*—Grace J. Fishel

[57] ABSTRACT

In an ultraviolet sterilizer unit a length of corrugated pipe is coiled into the shape of a helix around an ultraviolet germicidal source to maximize the exposure of the fluid media flowing in the pipe to the ultraviolet germicidal source. The pipe is formed of a tough, flexible fluorinated polyalkylene resin capable of being used without sidewall support, and has an internal groove.

14 Claims, 5 Drawing Sheets

STERILIZER UNIT FOR FLUID MEDIA AND PROCESS

The present invention relates to a sterilizer unit and to a process for sterilizing a fluid media.

Sterilizer units making use of ultraviolet radiation are used for sterilizing fluid media such as water for consumption, use or discharge into the environment. In earlier models, the fluid media was flowed through quartz or special glass pipes which are transparent to germicidal radiation but which become clouded with residue within a short time under normal operating conditions. Since a thin film of residue greatly reduces transparency it is necessary to clean the pipes frequently. This procedure is inefficient and not practical for a continuous operation since it requires shutting down the apparatus and draining the water to reach the inner surfaces of the tubing for cleaning.

The equipment described in U. S. Pat. Nos. 3,634,025 and 3,700,406 was a great improvement over that described above but it is big, expensive and, most importantly, does not give a particularly good kill rate. The sterilizer unit described in the subject patents includes a bank of parallel ultraviolet tubes between which the fluid media is flowed along a serpentine path. It involved the discovery that pipes made of fluorinated ethylene propylene copolymer are capable of transmitting ultraviolet radiation over an extended period of time without undergoing photochemical deterioration. The non-stick properties of polytetrafluoroethylene making possible the provision of pipes which do not cloud with residue were known before but the resistance of fluorinated ethylene propylene to photochemical deterioration in a sterilizer unit was not.

In accordance with the above, it is an object of the present invention to provide an ultraviolet sterilizer unit which has the desirable features of the prior art but which is more compact, less expensive and more effective. Other objects and features of the invention will be in part apparent and in part pointed out hereinafter.

In the accompanying drawings, in which one of various possible embodiments of the invention is illustrated, corresponding reference numerals refer to corresponding parts and in which.

Figure 1:
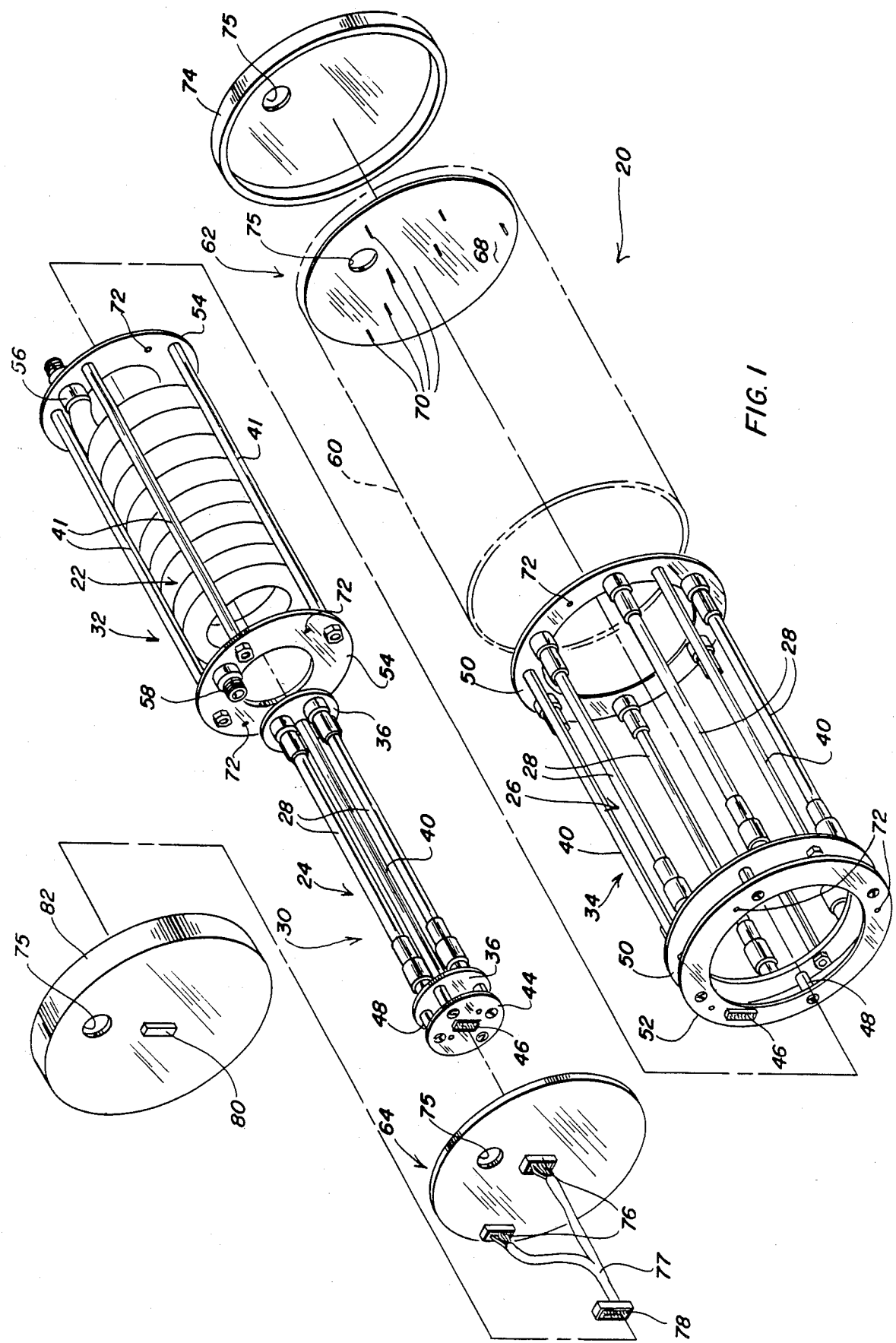
FIG. 1 is an exploded view of a sterilizer unit in accordance with the present invention.

Referring to the drawings more particularly by reference character, a sterilizer unit 20 in accordance with the present invention includes a coil of corrugated pipe 22 wrapped around a germicidal radiation source 24 into the shape of a helix. In the embodiment shown, a second radiation source 26 blankets pipe 22 so that the contents of the pipe are irradiated by a radiation source from the inside and the outside of the coil.

Germicidal radiation sources 24 and 26 preferably comprise a plurality of ultraviolet lamps 28 such that total failure of either radiation source by failure of all of the lamps is most unlikely. Lamps 28 are preferably tube shaped and pipe 22 is preferably mounted on telescoping, modular inner, middle and outer sections 30, 32 and 34 for simplicity of manufacture and maintenance as more particularly described hereinafter.

Figure 7:
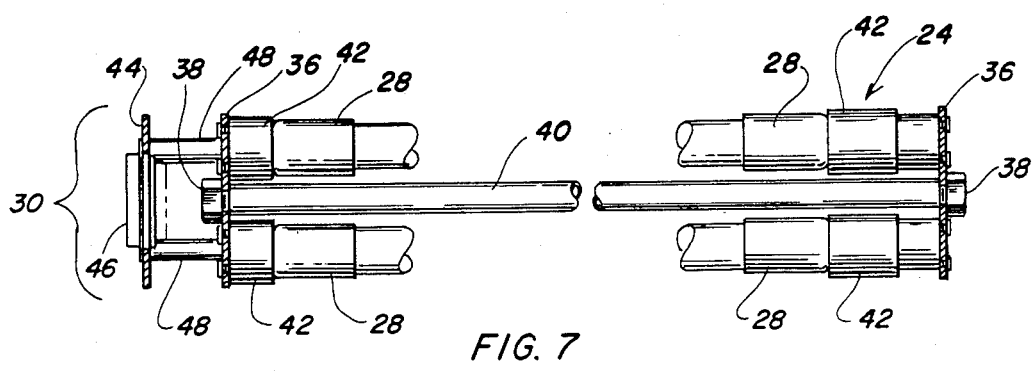
FIG. 7 is a side elevational view in cross section of the inner section.

As best seen in FIG. 7, inner section 30 includes a pair of circular end plates 36 joined by nut 38 to a hollow rod 40, the opposite ends of which are threaded. Lamps 28 making up germicidal radiation source 24 are mounted in supporting sockets 42 between circular end plates 36. Four lamps are shown in the particular embodiment illustrated, symmetrically disposed between said plates about the surface thereof. With continuing reference to FIG. 7, a circular electrical mounting plate 44 having the same diameter as end plates 36 and bearing electrical connector 46 is mounted on rods 48 to left plate 36. The electrical leads for sockets 42 on right hand plate 36, which for the purpose of clarity are not shown in the drawings, are threaded through hollow rod 40 and dressed with leads from sockets 42 on left hand plate 36, also not shown, for connection to electrical connector 46.

Figure 5:
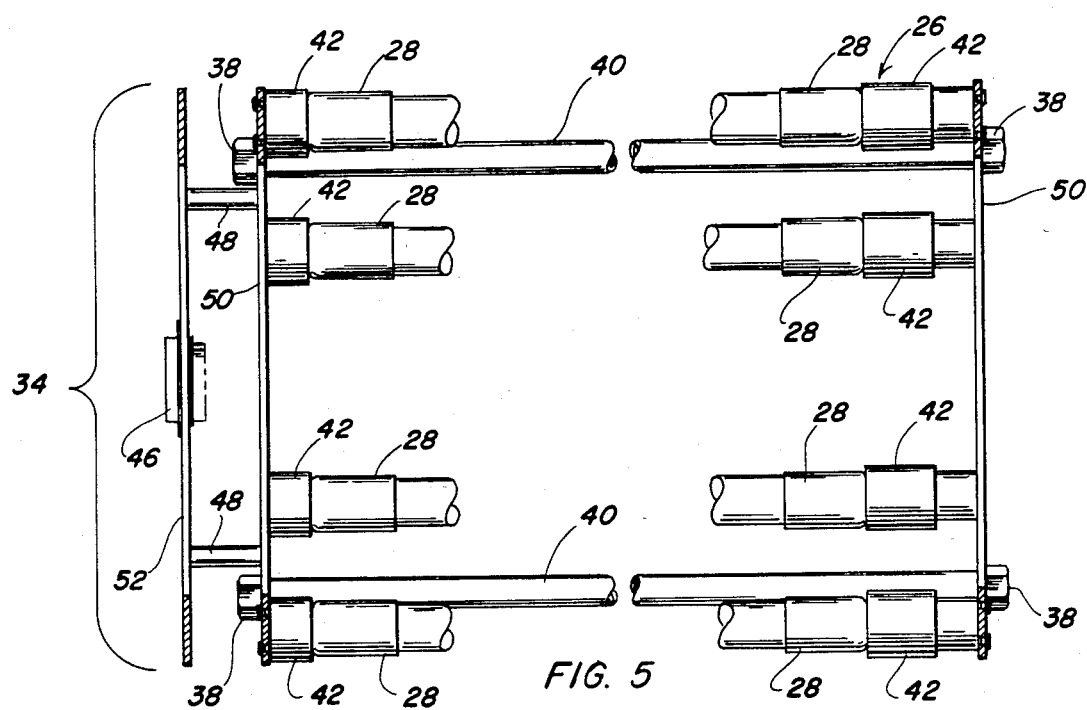
FIG. 5 is a side elevational view in cross section of the outer section of the sterilizer unit shown in FIG. 1.

The details of outer section 34 are shown in FIG. 5 and are similar to those of inner section 30 but differ in the following respects. Outer section 34 includes a pair of annular end plates 50 within which inner and middle sections 30 and 32 are telescoped. Annular end plates 50 are bound together by nuts 38 to four hollow rods 40 which are symmetrically arranged around each end plate 50. Six lamps 28 make up germidical radiation source 26 and are mounted in pairs about the inner surface of annular end plates 50 between adjacent rods 40 in supporting sockets 42. An annular electrical plate 52 having the same configuration as end plates 50 and bearing an electrical connector 46 is mounted on three rods 48 to left plate 50 as viewed in FIG. 5. The electrical leads (not shown) from sockets 42 on right plate 50 are threaded through hollow rods 40, and dressed with leads (not shown) from sockets 42 on left hand plate 50 for connection to electrical connector 46.

Figure 4:
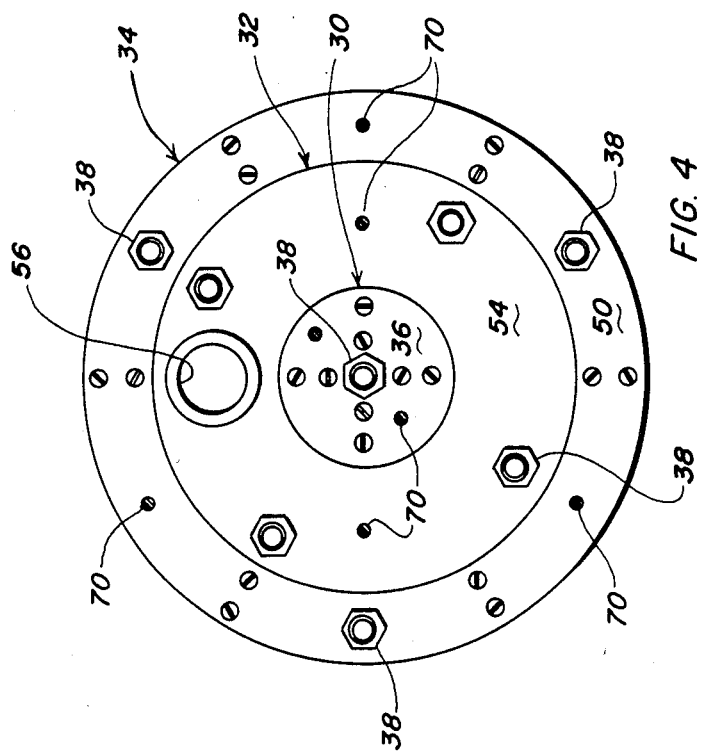
FIG. 4 is a sectional line taken along line 4—4 in FIG. 2.
Figure 3:
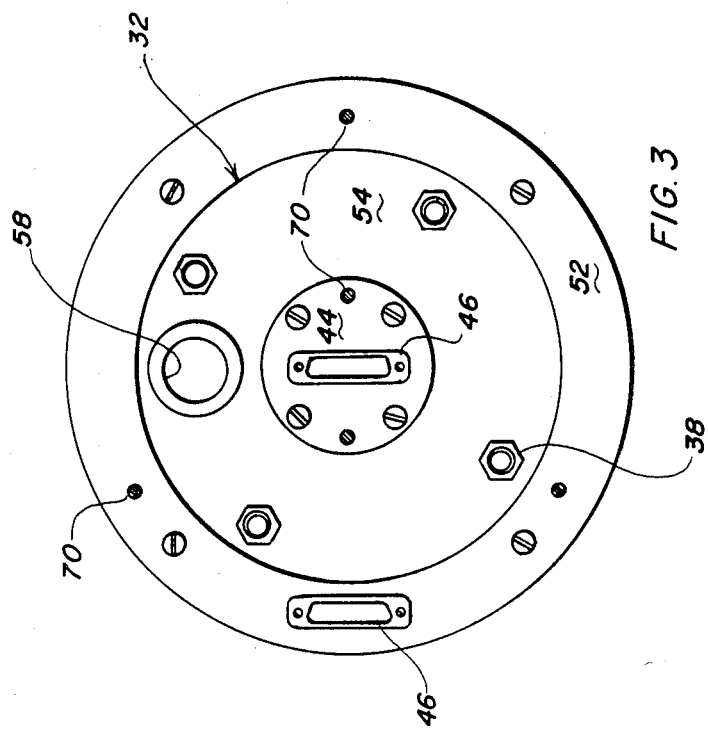
FIG. 3 is a sectional view taken along line 3—3 in FIG. 2.
Figure 6:
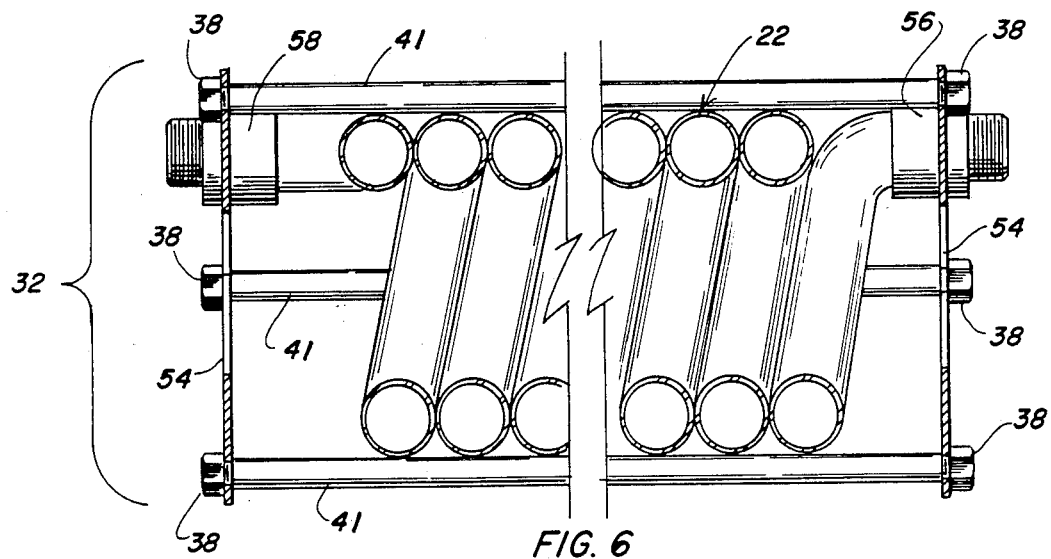
FIG. 6 is a side elevational view in cross section of the middle section.

Middle section 32 fits between inner and outer sections 30 and 34. Referring to FIG. 6 taken in connection with FIGS. 3 and 4, it is seen that middle section 32 includes a pair of annular end plates 54 which when assembled as shown in FIGS. 3 and 4, concentrically receive circular end plates 36 and are in turn received within annular end plates 50. End plates 54 are bound together by nuts 38 to four solid rods 41 which are symmetrically arranged around each end plate 54. In addition to joining end plates 54, rods 41 form a support for maintaining the diameter of helical coil of pipe 22. As best seen in FIG. 6, a first port 56 is provided in right hand end plate 54 and a second port 58 is provided in left hand end plate 54 through which fluid media is flowed. Ports 56 and 58 are preferably arranged such that they come from the same side of the helix into which pipe 22 is coiled.

Figure 2:
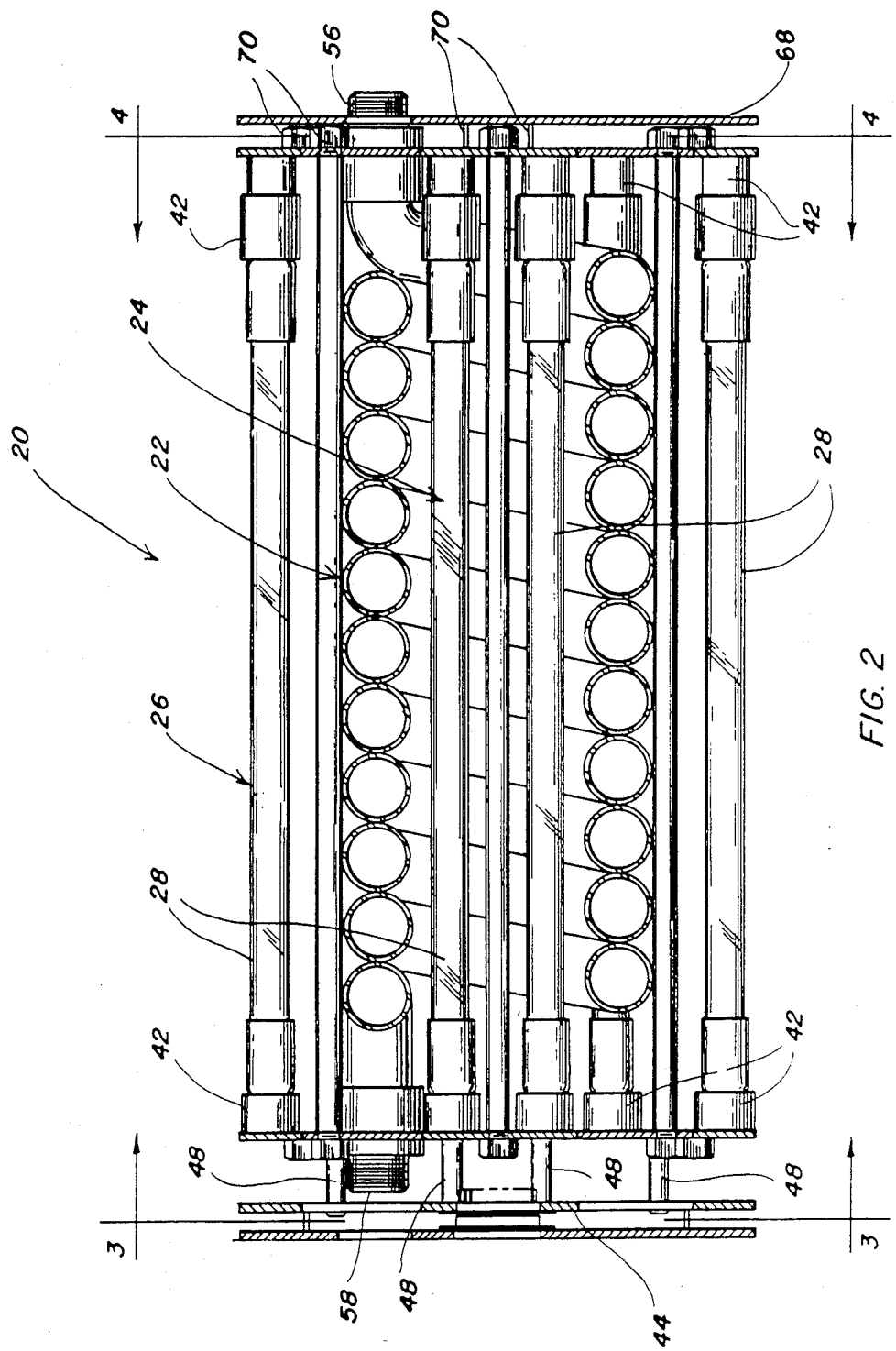
FIG. 2 is a side elevational view in cross section of the sterilizer unit shown in FIG. 1.

Inner, middle and outer sections 30, 32 and 34 are housed within cylindrical casing 60 which is sized to receive the assembled sections. A pair of bulkheads 62 and 64 are provided in casing 60 to align the sections during assembly and hold them during use. As shown in FIG. 2, the bulkhead at the right hand end of sections 30, 32 and 34 comprises a circular plate 68 which is fixed in casing 60 and which has a plurality of upstanding indexing pins 70 that are received during assembly of the unit in correspondingly aligned holes 72 in sections 30, 32 and 34 provided in end plates 36, 54 and 50, respectively. An end cap 74 completes the assembly at the right end of casing 60. A hole 75 is provided through end cap 74 and bulkhead 62 for connecting a pipe to port 56.

In addition to upstanding indexing pins 70, bulkhead 64 has mating electrical connectors 76 for attachment to the electrical connectors 46 carried by electrical mounting plates 44 and 52 such that when the indexing pins are received in correspondingly aligned holes 72 in sections 30, 32 and 34 located in end plates 36, 54 and 50, respectively, the electrical connectors on the bulkhead are mated with the electrical connectors on the electrical mounting plates. The electrical leads 77 from the mated connectors pass through bulkhead 64 and terminate in another electrical connector 78, a mate 80 to which is carried by end cap 82 located at the left end of casing 60 such that when the end cap is removed, the electrical circuit is broken. The electrical leads from connector 80 pass through the end cap and are routed to different ballasts (not shown) which are externally housed so that they will not be wetted if there is a leak in the system. Different ballasts are provided so that if one ballast fails, not all of the lamps on either the inner or outer section will fail. Hole 75 is provided through end cap 82 and bulkhead 64 for connecting a pipe to port 58.

The physical conformation and chemical nature of pipe 22 are very important for the purpose of accomplishing the objects of the present invention. To maximize the exposure of the fluid media to the germicidal radiation source, pipe 22 is preferably a thin walled, corrugated tube wound in a tight helix around radiation source 24 and formed of a tough, flexible fluorinated polyalkylene resin which is resistant to the buildup of film on the inner surface thereof and which remains transparent to ultraviolet rays over an extended period of time. Suitable tubing satisfying all of the above-mentioned criteria are described in the following Military Specification Sheets, which are incorporated by reference herein: MIL-T-81914/6(AS), dated July 14, 1976, for ethylene-tetrafluoroethylene and in MIL-T-81914/4(AS), dated Feb. 28, 1973 for fluorinated ethylene propylene. While either ethylene-tetrafluoroethylene or fluorinated ethylene propylene can be used, the performance characteristics of ethylene-tetrafluoroethylene are superior in all respects.

For use in the present invention, pipe 22 must be sufficiently tough to withstand the pressure of the fluid being flowed through the sterilizer unit but, on the other hand, thin walled enough not to interfere with the transmissibility of the ultraviolet light. When the pipe 22 is formed of ethylene-tetrafluoroethylene or fluorinated ethylene propylene, tubing having a wall thickness as set forth in the above mentioned specifications may be used. The diameter of pipe 22 is also critical since germicidal efficiency is dependent not only on the thickness of the walls but also on the transmissibility of the fluid being treated and on the output of lamps 28. When unit 20 is as shown in the drawings and when each lamp 28 is in the range of 15 to 65 watts, pipe 22 should not be larger than about 1.5 inches in diameter. While a smaller pipe can be used and favors a better kill, it reduces the volume of fluid being sterilized and limits the volumetric flow from the sterilizer unit. A larger pipe favors volumetric flow but compromises the bacterial reduction. Longer residence times of the fluid media in the presence of the germicidal radiation source increase the kill rate. Since the length of lamps 28 generally correlates with the wattage and the length of pipe 22 which can be wound around lamps 28 depends of the length of the lamps, the residence time of the fluid media can be regulated by the selection of the lamps to that amount which is sufficient to reduce the bacterial count to an acceptable level.

Figure 8:
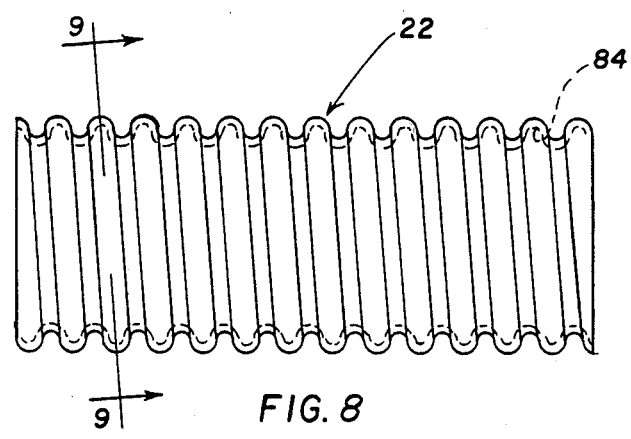
FIG. 8 is a side elevational view of a corrugated pipe having helical grooves.
Figure 9:
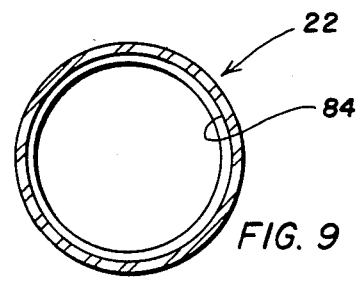
FIG. 9 is a sectional view taken along line 9—9 in FIG. 8.
Figure 10:
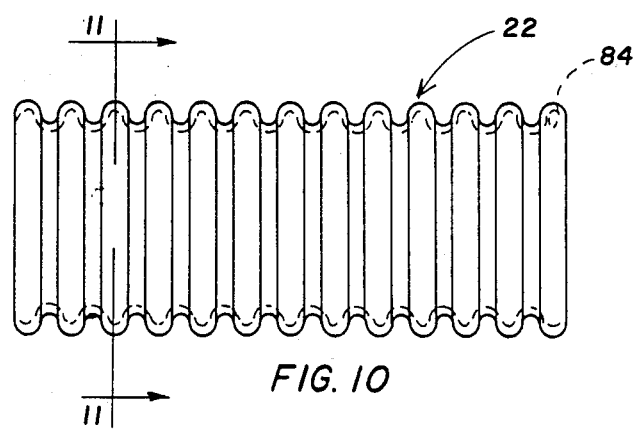
FIG. 10 is a side elevational view of a corrugated pipe having annular grooves; and, FIG. 11 is a sectional view taken along line 11—11 in FIG. 10.
Figure 11:
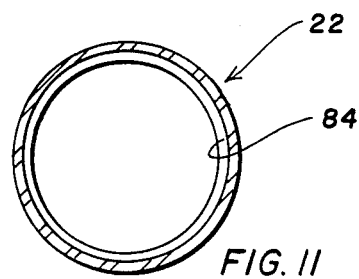

In addition to being tough, pipe 22 must be flexible such that it can be bent into a tight helix around lamps 28. For this purpose, pipe which is useful in the present invention has a minimum bend radius of at least 4 inches. Many grades of fluorinated ethylene propylene or the like are unsuitable for use in the present invention because they lack the required degree of flexibility. As shown in FIGS. 1, 2 and 6, pipe 22 is wound with adjacent coils of pipe touching each other around a radius which is slightly larger than that of inner section 30, preferably no more than about ¼ inch larger. While pipe 22 can be coiled less tightly depending on the bacterial kill required, the configuration described above is preferred because it increases the germicidal efficiency of the unit by maximizing the intensity of the light received by the pipe 22 and the available energy absorbed by the fluid being sterilized. Pipe 22 is also corrugated with internal grooves 84 which are generally transverse to the flow of fluid through the pipe. Grooves 84 are preferably helical as shown in FIGS. 8 and 9 or annular as shown in FIGS. 10 and 11. Grooves 84 function to churn the media as it flows through the pipe so that all of the media comes into close proximity to the walls of the tube for a more homogeneous kill.

In the embodiment illustrated in the drawings, there are no joints or seams in pipe 22 between ports 56 and 58 thus eliminating the potential for leakage. In use, fluid media is passed through pipe 22 between ports 56 and 58 while the media is simultaneously exposed to ultraviolet germicidal radiation from radiation sources 24 and 26 along the entire length of the pipe. As the fluid media flows through pipe 22, grooves 84 churn the media so that all of it comes in close proximity to the walls of the pipe for a more homogeneous kill. The flow rate through pipe 22 and distance traveled are adjusted such that the desired reduction in bacterial count occur.

In view of the above, it will be seen that the several objects of the invention are achieved and other advantageous results attained. As various changes could be made in the above constructions and methods without departing from the scope of the invention it is intended that all matter contained in the above description or shown in the accompanying drawings shall be interpreted as illustrative and not in a limiting sense.

What is claimed is:

1. A process of sterilizing a fluid media comprising the steps of:
   (a) providing a length of thin walled corrugated pipe in the shape of a helix coiled around an ultraviolet germicidal radiation source, said corrugated pipe being formed of a tough, flexible fluorinated polyalkylene resin which is resistant to buildup of film on the inner surface thereof, which remains transparent to ultraviolet rays over an extended period of time and which is capable of being used without sidewall support;

(b) passing fluid media through the corrugated pipe; and, (c) simultaneously exposing the fluid media to ultraviolet germicidal radiation by irradiating the fluid media through the walls of said corrugated pipe with said germicidal radiation source.

2. The process of claim 1 wherein the corrugated pipe has a wall thickness between about 0.013 and about 0.023 inch.

3. The process of claim 1 wherein the corrugated pipe is wound with adjacent coils of said corrugated pipe touching each other around a radius which is slightly larger than the diameter of the germicidal radiation source whereby the intensity of the light received by the corrugated pipe and the available energy absorbed by the fluid media is maximized.

4. The process of claim 3 wherein the corrugated pipe has an internal groove which is annular or helical.

5. The process of claim 4 wherein the corrugated pipe is formed of ethylene-tetrafluoroethylene copolymer.

6. A sterilizer unit comprising a length of thin walled corrugated pipe coiled into the shape of a helix around a germicidal radiation source with adjacent coils of said corrugated pipe is close proximity to each other around a radius which is slightly larger than that of the germicidal radiation source and is formed of a tough, flexible fluorinated polyalkylene resin which is resistant to buildup of film on an inner surface thereof, which remains transparent to ultraviolet rays over an extended period of time and which is capable of being used without sidewall support.

7. The sterilizer unit of claim 6 wherein the corrugated pipe has a wall thickness between about 0.013 and about 0.023 inch.

8. The sterilizer unit of claim 6 wherein the corrugated pipe has an internal groove which is annular or helical.

9. The sterilizer unit of claim 8 wherein the corrugated pipe is formed of ethylene-tetrafluoroethylene copolymer.

10. A sterilizer unit comprising telescoped inner, middle and outer sections, said inner section having a plurality of germicidal radiation lamps about an outer surface thereof, said middle section supporting the inner section and having a length of thin walled corrugated pipe coiled into the shape of a helix with adjacent coils of said corrugated pipe in close proximity to each other wrapped around a radius which is slightly larger than the radius of the middle section, said corrugated pipe being formed of a tough, flexible fluorinated polyalkylene resin which is resistant to buildup of film on an inner surface thereof, which remains transparent to ultraviolet rays over an extended period of time and which is capable of being used without sidewall support, said outer section supporting the middle section and having a plurality of germicidal radiation lamps about an inner surface thereof.

11. The sterilizer unit of claim 10 wherein the corrugated pipe has a wall thickness between about 0.013 and about 0.023 inch.

12. The sterilizer unit of claim 10 wherein the corrugated pipe has an internal groove substantially transverse to a main axis of the helix into which said corrugated pipe is coiled.

13. The sterilizer unit of claim 12 wherein the corrugated pipe has a minimum bend radius of at least four inches.

14. The sterilizer unit of claim 13 wherein the corrugated pipe is formed of ethylenetetrafluoroethylene copolymer.

* * * * *